(12) United States Patent
Scheller et al.

(10) Patent No.: US 10,532,189 B2
(45) Date of Patent: Jan. 14, 2020

(54) CONTROLLED EXPANSION BALLOON CATHETER

(75) Inventors: Bruno Scheller, Saarbrucken (DE); Ulrich Speck, Berlin (DE)

(73) Assignee: Invatec Technology Center GmbH, Frauenfeld (CH)

( * ) Notice: Subject to any disclaimer, the term of this patent is extended or adjusted under 35 U.S.C. 154(b) by 1941 days.

(21) Appl. No.: 12/675,394

(22) PCT Filed: Aug. 26, 2008

(86) PCT No.: PCT/DE2008/001456
§ 371 (c)(1),
(2), (4) Date: Sep. 8, 2010

(87) PCT Pub. No.: WO2009/026914
PCT Pub. Date: Mar. 5, 2009

(65) Prior Publication Data
US 2010/0324648 A1 Dec. 23, 2010

(30) Foreign Application Priority Data
Aug. 29, 2007 (DE) .......... 10 2007 040 868

(51) Int. Cl.
*A61F 2/95* (2013.01)
*A61F 2/06* (2013.01)
*A61M 25/10* (2013.01)

(52) U.S. Cl.
CPC ................ *A61M 25/10* (2013.01)

(58) Field of Classification Search
CPC ............ A61F 2/95; A61F 2002/9528; A61F 2002/9534; A61F 2/954; A61F 2/958; A61F 2002/9583; A61F 2/962; A61F 2/966; A61F 2002/30019; A61F 2250/0048; A61F 2/92; A61F 2/06; A61F 2/84; A61M 25/104; A61M 25/10; A61M 29/00; A61B 17/12118
See application file for complete search history.

(56) References Cited

U.S. PATENT DOCUMENTS 3,736,939 A * 6/1973 Taylor ................... A61M 25/10
604/265
5,049,138 A * 9/1991 Chevalier ............. A61L 29/041
604/265
(Continued)

FOREIGN PATENT DOCUMENTS

CA 2 372 820 3/2002
DE 102004046244 3/2006
(Continued)

OTHER PUBLICATIONS

PCT International Search Report for PCT/DE2008/001285 filed on Aug. 26, 2008 in the name of Bruno Scheller, et al.
(Continued)

*Primary Examiner* — Vi X Nguyen

(57) ABSTRACT

The invention relates to a drug-coated balloon catheter which has a catheter balloon mounted on its distal end and an expansion protection surrounding the same. The invention is characterized in that the catheter balloon is protected from premature expansion even under strong mechanical stress and in that the catheter balloon folds back more easily after dilation.

18 Claims, 1 Drawing Sheet

(56) References Cited

U.S. PATENT DOCUMENTS

| | | | |
|---|---|---|---|
| 5,102,402 A | 4/1992 | Dror et al. | |
| 5,158,548 A * | 10/1992 | Lau | A61F 2/92 606/194 |
| 5,234,457 A * | 8/1993 | Andersen | 606/198 |
| 5,304,121 A | 4/1994 | Sahatjian | |
| 5,370,614 A | 12/1994 | Amundson et al. | |
| 5,401,257 A * | 3/1995 | Chevalier, Jr. | A61M 25/0017 604/265 |
| 5,514,112 A * | 5/1996 | Chu | A61M 27/00 604/265 |
| 5,527,282 A * | 6/1996 | Segal | 604/104 |
| 5,545,209 A * | 8/1996 | Roberts et al. | 623/1.11 |
| 5,571,086 A * | 11/1996 | Kaplan et al. | 604/96.01 |
| 5,603,698 A * | 2/1997 | Roberts | A61F 2/95 604/104 |
| 5,823,198 A * | 10/1998 | Jones et al. | 128/899 |
| 5,843,092 A * | 12/1998 | Heller et al. | 606/108 |
| 5,860,916 A * | 1/1999 | Pylant | A61M 3/0258 600/114 |
| 5,868,708 A * | 2/1999 | Hart et al. | 604/104 |
| 5,893,840 A | 4/1999 | Hull et al. | |
| 5,902,333 A * | 5/1999 | Roberts | A61F 2/95 606/191 |
| 5,908,448 A * | 6/1999 | Roberts et al. | 623/1.23 |
| 5,984,964 A * | 11/1999 | Roberts | A61F 2/95 604/104 |
| 6,071,300 A * | 6/2000 | Brenneman | A61B 17/0057 604/265 |
| 6,077,275 A * | 6/2000 | Bryars | A61B 17/12013 606/139 |
| 6,249,952 B1 * | 6/2001 | Ding | 29/460 |
| 6,306,166 B1 | 10/2001 | Barry et al. | |
| 6,369,039 B1 | 4/2002 | Palasis et al. | |
| 6,383,144 B1 * | 5/2002 | Mooney | A61B 1/012 600/435 |
| 6,425,898 B1 * | 7/2002 | Wilson | A61F 2/966 606/108 |
| 6,602,280 B2 * | 8/2003 | Chobotov | A61F 2/07 606/108 |
| 6,616,650 B1 | 9/2003 | Rowe | |
| 6,673,058 B2 * | 1/2004 | Snow | A61J 15/0023 128/898 |
| 6,884,257 B1 * | 4/2005 | Cox | A61F 2/958 604/103.05 |
| 6,913,765 B2 * | 7/2005 | Li | A61F 2/04 424/426 |
| 7,004,962 B2 * | 2/2006 | Stinson | A61B 17/12022 604/265 |
| 7,104,684 B2 | 9/2006 | Felder | |
| 7,105,018 B1 | 9/2006 | Yip et al. | |
| 7,588,825 B2 * | 9/2009 | Bell et al. | 428/402 |
| 8,226,701 B2 * | 7/2012 | Glynn | A61F 2/91 623/1.11 |
| 2001/0004696 A1 * | 6/2001 | Roberts | A61F 2/95 606/108 |
| 2002/0111601 A1 * | 8/2002 | Thompson | A61M 5/14276 604/514 |
| 2002/0151844 A1 | 10/2002 | Yang et al. | |
| 2002/0165521 A1 | 11/2002 | Cioanta et al. | |
| 2003/0064965 A1 | 4/2003 | Richter | |
| 2003/0181973 A1 | 9/2003 | Sahota | |
| 2003/0233101 A1 * | 12/2003 | Lubock | A61M 37/0069 606/116 |
| 2004/0215312 A1 * | 10/2004 | Andreas | 623/1.11 |
| 2004/2024003 | 11/2004 | Schultz | |
| 2005/0033417 A1 | 2/2005 | Borges et al. | |
| 2005/0059965 A1 | 3/2005 | Eberl et al. | |
| 2005/0209674 A1 * | 9/2005 | Kutscher et al. | 623/1.11 |
| 2006/0002973 A1 | 1/2006 | Barry | |
| 2006/0034894 A1 | 2/2006 | Lakkis | |
| 2006/0085065 A1 | 4/2006 | Krause et al. | |
| 2007/0003596 A1 | 1/2007 | Tittelbach et al. | |
| 2009/0264858 A1 * | 10/2009 | Nash | A61M 25/0069 604/508 |

FOREIGN PATENT DOCUMENTS

| | | |
|---|---|---|
| DE | 102004048265 | 4/2006 |
| EP | 1140273 | 6/2005 |
| EP | 0519063 | 7/2010 |
| WO | WO 9423786 A1 * | 10/1994 ............ A61M 29/00 |
| WO | 98/03083 | 2/1995 |
| WO | 95/11055 | 4/1995 |
| WO | 9511055 | 4/1995 |
| WO | 96/39949 | 12/1996 |
| WO | 99/08729 | 2/1999 |
| WO | 00/10622 | 3/2000 |
| WO | 00/21584 | 4/2000 |
| WO | 00/32267 | 6/2000 |
| WO | 0152772 | 7/2001 |
| WO | 02/076509 | 10/2002 |
| WO | 03039612 | 5/2003 |
| WO | WO 2003/039345 A2 | 5/2003 |
| WO | 204/006976 | 1/2004 |
| WO | 2004/022124 | 3/2004 |
| WO | 2004/028582 | 4/2004 |
| WO | 2004/028610 | 4/2004 |
| WO | WO 2004/091441 A3 | 10/2004 |
| WO | WO 2005023153 A2 * | 3/2005 ............... A61F 2/06 |
| WO | 05089855 | 9/2005 |
| WO | 2007/008829 | 1/2007 |
| WO | 07008829 | 1/2007 |
| WO | 2008/063576 | 5/2008 |

OTHER PUBLICATIONS

PCT Written Opinion for PCT/DE2008/001285 filed on Aug. 26, 2008 in the name of Bruno Scheller, et al. (translation).

Hayakawa E., et al., Viscosity Study on Self-Association of Doxorubicin in Aqueous Solution, Chemical Pharm. Bulletin 1991; 39:1282-1286.

Kutryk M. et al., Local Intracoronary Administration of Antisense Oligonucleotide Against C-MYC for the Prevention of In-stent Restenosis: Results of the Randomized Investigation by the Thoraxcenter of Antisense DNA Using Local Delivery and IVUS After Coronary Stenting Trial, J. Am. Coll. Cardiol. 2002; 39:281-287.

Kiesz R. et al., Local Delivery of Enoxaparin to Decrease Restonsis After Stenting: Results of Initial Multicenter Trial: Polish-American Local Lovenox NIR Assessment Study, Circulation 200; 103:26-31.

Muni N. et al., Coronary Drug-elating Stent Development: Issues in Trial Design, Am Heart J 2005; 149:415-433.

Scheller B. et al., Prevention of Restenosis: Is Angioplasty the Answer?, Heart 2007; 93:539-541.

Scheller B. et al., Treatment of Coronary In-stent Restenosis with a Paclitaxel-Coated Ballon Catheter, N Engl J Med 2006; 255: 2113-2124.

Schillinger M. et al., Balloon Angioplasty versus Implantation of Nitinol Stents in the Superficial Femoral Artery, N Engl J Med 2006; 354: 1879-1888.

Scheller B. et al., Paclitaxel Balloon Coating, a Novel Method for Prevention and Therapy of Restenosis, Circulation 2004; 110: 810-814.

Tepe G. et al., Local Delivery of Paclitaxel to Inhibit Restenosis during Angioplasty of the Leg N Engl J 2008; 358: 689-699.

Levin A. et al., Specific Binding to Intracellular Proteins Determines Arterial Transport Properties for Rapamycin and Paclitaxel PNAS 2004; 101: 9463-9467.

Yang W. et al., Arsenic Trioxide Eluting Stent Reduces Neointima Formation in a Rabbit Iliac Artery Injury Model Cardio Res 2006; 72: 483-493.

Cremers, B., et al., V1742—Paclitaxel-beschichtete PTCA-Katheter: Gibt es Unterschiede? Einfluss von PACCOCATH®-und DIOR®-Ballonkathetern auf die Neointimaproliferation an Schweinekoronarien, Clinical Research in Cardiology 2008, 97—Suppl 1.

(56) References Cited

OTHER PUBLICATIONS

PCT International Search Report for PCT/DE2008/001456 filed on Aug. 26, 2008 in the name of Innora GMBH.
PCT Written Opinion for PCT/DE2008/001456 filed on Aug. 26, 2008 in the name of Innora GMBH.

* cited by examiner

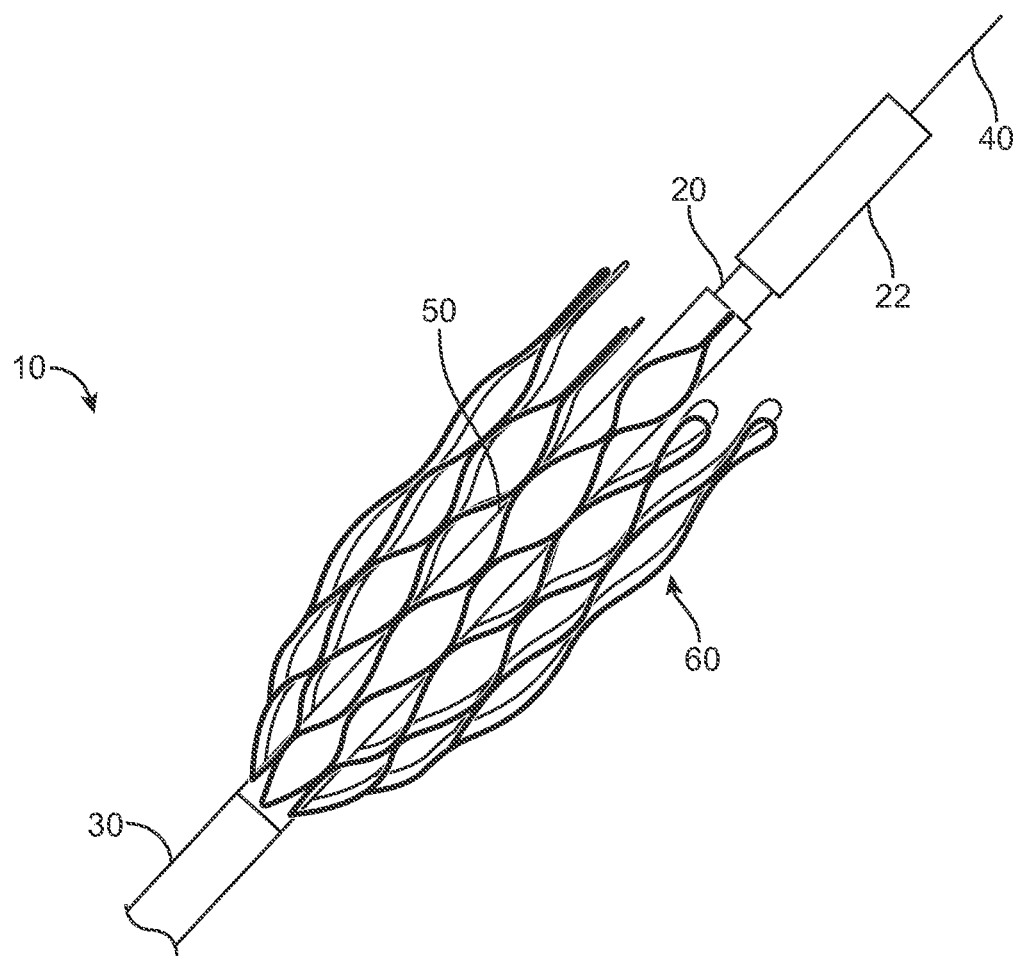

CONTROLLED EXPANSION BALLOON CATHETER

CROSS REFERENCE TO RELATED APPLICATIONS

The present application is the US national stage of International Application PCT/DE2008/001456 filed on Aug. 26, 2008 which, in turn, claims priority to German Application 102007040868.6, filed on Aug. 29, 2007. This application may be related to U.S. patent application Ser. No. 12/671,910 filed on Feb. 2, 2010.

This invention concerns a balloon catheter coated with at least one active substance including a distally assembled catheter balloon and an expandable protection against expansion which surrounds this where the catheter balloon is on the one hand protected against premature unfolding even when it experiences conditions of severe mechanical stress and on the other hand the catheter balloon can demonstrate that it can refold itself better after dilatation has taken place.

Catheters are tubes of different lengths or else other elongated objects for the transfer of materials, proximally fitted with a grip and/or an attachment for fitting various instruments, extensions or vessels. Distally they are either open or closed, and they can either be with or without components which can perform different functions. Catheters are used to carry out various interventions and perform various functions within the body. A very useful type of catheter contains a balloon in the distal area. The balloon is normally delivered to the target location in a folded or contracted state. It can be expanded by filling with a fluid under a slight pressure or under a high pressure. In this way the catheter can be fixed in position and can be used for creating or expanding cavities in the body's natural passages, blood vessels, body cavities and also in solid tissue. The expansion of coronary arteries with balloon catheters is known as percutaneous transluminal coronary angioplasty (PTCA), the expansion of other arteries is generally known as percutaneous angioplasty (PTA). The balloon can be used to carry chemical substances, radioisotopes, pharmaceuticals, diagnostic agents or to carry other useful substances or perform other useful functions.

STATE OF THE ART

Balloons with specific external dimensions are made from materials that are slightly elastic. They are delivered to the location in a folded condition and are usually rolled up. Here they are expanded to their predetermined sizes by insufflation with a fluid which is normally a diluted contrast medium. It is extremely advantageous to have a very small diameter which can be achieved by folding the balloon tightly. The folds are not particularly well secured in the balloon catheters that are in normal use today. They can become loose and even open completely when being handled and when being passed through insertion sheaths and guide catheters. After use the fluid from the balloon is sucked from the balloon using a vacuum; the balloon's cross-sectional area is reduced, but it does however remain unfolded. Premature loosening of the folds increases the cross-sectional area of the balloon in an undesirable manner and can lead, for example, in cases of balloons coated with pharmaceuticals to the premature release of at least part of the active substance.

The lack of tightness in the folding causes certain measures to be necessary to prevent the premature delivery of the coating and severely restricts the choice of coating materials available. In particular liquid media and active substances that are readily soluble in water have previously not been suitable, because these are washed away e.g. by the blood stream before the balloon reaches the target area.

Balloon catheters can be provided with stents. Stents are tube-shaped metal or plastic structures which can be pushed over the folded balloon and keep them tightly folded until they are expanded using high pressure in the constricted section of the vessels where treatment is required. In so doing the stents expand radially. They stabilize the constricted blood vessels against any elastic restorative forces and at the same time secure any detached parts of the vascular wall (dissections). In order to achieve this, the stents are characterized by the highest possible resistance to radial pressure. Where balloon catheters are provided with preassembled stents there are no problems with premature unfolding of the balloons.

With many applications of balloon catheters the implantation of stents is however not required, or it can actually be harmful.

The following techniques have been known about previously which prevent premature loosening of folding or which were introduced to improve the adhesion of substances to balloon catheters and which reduce their premature diffusion into the surrounding medium Previously assembled expandable stents fitted to the folded balloons hold the folds in place until the balloon is inflated at the site of the stenosis, causing the stent to expand and press against the vascular wall. The stent remains in the vessel after deflation of the balloon in order to prevent constriction taking place because of the elastic properties of the vascular wall, and if necessary to push any detached layers (dissections) onto the vascular wall on a long term basis. Protective tubes are used to prevent any displacement of the balloon expandable stents located on the folded balloons. These protective tubes extend over the entire length of the catheter from the distal of the stent to the proximal end of the catheter (e.g. CA 2 372 820). The protective tube is pulled back before the expansion of the stent. Protective tubes of different kinds have been used previously with self expanding stents where a stent which is compressed to a small diameter by means of the protective tube is released by pulling back the protective tube. The self expanding stent expands to a greater diameter on its own and comes into position alongside the vascular wall.

The use of physiologically compatible saturated aqueous solutions for localised treatments using catheters is proposed in EP 1 140 273. The use of protective tubing or polymers which adhere to the catheters and absorb the solution are proposed as measures to be taken against the premature washing away of the solutions from expandable catheters.

According to U.S. Pat. No. 6,616,650 a guide catheter is used as protection for a balloon provided with a stent and coated with a pharmaceutical product where the balloon is only released from the guide catheter immediately before expansion in the stenosis.

In U.S. Pat. No. 7,104,684 porous coverings or sleeves are described which are made from PTFE, for example, and which surround the folded balloon. The pharmaceutical product or a solution containing it is located between the membrane of the balloon and the covering; the product or solution is pressed out through the pores in the covering by the balloon as it expands.

U.S. Pat. No. 5,370,614 A1 describes a balloon with a viscous coating which is protected against premature detachment by the use of a thin-walled covering containing a preformed longitudinal seam. When the balloon is expanded the covering splits along the preformed seam and covers a long section of the vascular wall so that this does not come in contact with the viscous coating.

A further version involving coverings which split is described in US 2002/0 151 844 where there is a surface layer made from an inelastic material which is impervious to the pharmaceutical product and which becomes torn in many places when the balloon is expanded. The pharmaceutical product is washed out through these tears. U.S. Pat. No. 5,102,402 describes balloons with specially made depressions (or folds) in the covering of the balloon. Microcapsules can be held within these folds. When the balloon is expanded the folds open out and the microcapsules are released to their surroundings.

In WO 2000/010622 A materials with rough surfaces are described for use in balloons. Pharmaceutical products should adhere to these. Many other patent specifications describe the use of hydrogels or other polymers or coating materials for improving the adhesion of pharmaceutical substances to the surfaces of the balloons and to delay the release of the active substances (e.g. U.S. Pat. No. 5,304, 121WO 9639949, WO 9908729, U.S. Pat. No. 6,306,166, US 2005/0033417), or which describe the use of coatings which are sparingly soluble in water or oily (WO 02076509).

Protection against a rapid premature release of the active substance is provided in several ways according to WO 00/21584 by selecting a sparingly water-soluble active substance which is embedded within a polymer and where there is in addition a protective tube which extends over the distal expandable section of the balloon catheter.

The measures previously described do not solve the problem of premature detachment of coatings of pharmaceutical substances from balloon catheter membranes into the blood. Guide catheters or protective tubes which are open at the distal end become filled with blood which flows backwards or forwards depending on the pressure conditions on the coated balloon. The position of the protective tube with respect to the balloon is either uncertain or difficult to control. Liquid and highly viscous coatings are less chemically stable in long term storage than solid preparations and are more difficult to sterilize. Finally coverings which peel off or become torn have the disadvantage that parts of the vascular wall are covered by the remains of the covering and are therefore not accessible to the pharmaceutical product and as in the case of US 2002/0 151 844 fragments of covering can lead to embolism of the vessels.

DESCRIPTIONS OF THE FIGURES

FIG. 1 is a perspective view of one embodiment of a balloon catheter 10 as described herein including a catheter shaft 20, a distal end 22, a protective tube 30, a guidewire 40, a catheter balloon 50 on the catheter shaft 20, and a stent 60.

DESCRIPTION OF THE INVENTION

The purpose of this invention is to prepare balloon catheters with distally assembled catheter balloons where the catheter balloon is on the one hand protected against premature unfolding even when it experiences conditions of severe stress and on the other hand the catheter balloon can demonstrate that it can refold itself better after it has dilated.

It is furthermore the purpose of this invention to minimise the loss in active substances which takes place amongst other things by the premature unfolding of balloons coated with medicinal products.

The purpose of this invention is achieved by the teachings of the independent patent claims. Preferred embodiments are disclosed in the dependent patent claims, the diagrams, the descriptions and in the examples.

The problem is that balloon catheters with distally assembled catheter balloons with a largely predetermined size in terms of their length and diameter, as used in percutaneous transluminal angioplasty (for example), in cases of mechanical stress tend towards a premature unfolding of the catheter balloon and this should be avoided.

A further problem is that the refolding of the catheter balloon is inadequate and that following dilatation only a partial refolding is possible because of the vacuum being used so that a catheter balloon generally has a greater diameter when withdrawn from the body than it had when it was introduced, which leads to complications when constricted sections of vessels must be negotiated. For example, this situation applies when a catheter balloon must be passed through a stent which has already been placed in position.

This invention therefore concerns a balloon catheter coated with at least one active substance, which includes a method of protection against expansion and a balloon coated in at least one active substance where the method of protection against expansion used protects the compressed catheter balloon against premature expansion until the moment when the catheter balloon actually does expand and if required can assist in the refolding of the balloon after it has been expanded.

This can basically be effected in two ways. One way is when a rigid, largely rigid or solid protective covering is pushed onto the catheter balloon and which prevents an expansion of the catheter balloon and an exchange of fluids with the surroundings as long as the covering is in position over the catheter balloon. These kinds of protective coverings are preferably in the form of a solid pipe or a solid tube and should preferably enclose the entire length of the catheter balloon. They should preferably contain a distally mounted seal to prevent or limit the exchange of blood with the lumen of the protective covering through which the catheter balloon is able to be pushed. One such seal can consist of a valve with, for example, 2 to 5 valve lips, or a thin perforated or perforatable membrane, or a soluble sealing material. Another possibility consists of an elastic protection against expansion which preferably does not completely cover the catheter balloon i.e. the surface of the catheter balloon and preferably only covers it to a small extent. It is therefore preferable that it demonstrates a perforated structure. This elastic protection against expansion is expanded during dilatation together with the catheter balloon. In addition to its elasticity this protection against expansion also demonstrates a restorative force which in the subsequent deflation of the catheter balloon substantially returns the catheter balloon to its original size i.e. the original diameter of the catheter balloon before dilatation is substantially restored.

Substantially restored to the original size or substantially restored to the original diameter means that the increases in diameter of the catheter balloon after expansion and deflation compared to the diameter before expansion are a maximum of 30% greater, and preferably a maximum of 20%, and more preferably a maximum of 10%, and even more preferably a maximum of 5% greater i.e. on removing the catheter balloons from the body these FIGURES are the maximum percentage increases in size or in thickness compared to when they were inserted into the body.

Basically the diameter of the catheter balloon with the protection against expansion is smaller after expansion and deflation than the diameter of the catheter balloon without the protection against expansion after expansion and deflation.

It should be noted that the terms 'expansion', 'inflation', 'dilatation', 'insufflation' or 'widening' all refer to the same thing which is the stretching or blowing up of the catheter balloon by applying a pressure from inside i.e. the inside of the catheter balloon which generally occurs by filling the catheter balloon with a contrast medium.

The terms 'deflation', 'refolding' or 'compressing' on the other hand refer to the opposite process which is the contraction or emptying of the catheter balloon by the application of a vacuum to the inside i.e. the inside of the catheter balloon which generally involves removing the contrast medium by suction.

After deflation of the catheter balloon the protection against expansion is preferably withdrawn from the body along with the catheter balloon. The protection against expansion is therefore preferably firmly or flexibly attached to the catheter balloon in such a way that when the catheter balloon is removed from the body the protection against expansion remains in place around the catheter balloon.

Furthermore the protection against expansion preferably possesses a radio-opaque marker at the distal end or the proximal end, or a distal end and the proximal end With a protection against expansion which is mounted so that it can move translationally along the axis of the catheter balloon the radio markers on the catheter balloon together with those located on the protection against expansion show the relative positions of the catheter balloon and the protection against expansion. As a result in the imaging process e.g. X-ray process a doctor can detect the positions of the catheter balloon and the protection against expansion and determine to what extent the protection against expansion still surrounds the catheter balloon along the longitudinal axis of the catheter or the longitudinal axis of the catheter balloon.

Either a perforated or a continuous protection tube can act as a protective tube. A continuous i.e. solid protection against expansion in the form of a flexible tube is then preferred to a perforated protective tube if there is a coated catheter balloon inside the protective tube either with or without a preassembled coated or uncoated stent, or if there is an uncoated catheter balloon with a preassembled coated stent. Non-perforated protective tubes are preferred that are designed in such a way that blood or other bodily fluids cannot penetrate into the lumen of the tube or where an exchange of fluids is at least significantly impeded. For this purpose, for example, a valve is provided distally. For example, a lip-shaped or flap-like arrangement of the distally tapered and laterally split tube is suitable for use as the distal valve mechanism. Here there can be 2 flaps, but there can however be 3 or more flaps present. The tube can also be sealed distally by means of soluble pharmaceutically and physiologically inactive substances. Examples of these kinds of substances are endogenous substances such as sugar or amino acids but they can also be polysaccharides, contrast media such as iodized X-ray contrast media. In each case the substances are in solid form. Sealing with contrast media has the advantage that their presence can be continually visualised during the intervention. Alternatively or additionally the tube can be provided with a seal or a valve fitted proximally that can seal the space between the catheter shaft and the tube. Suitable sealing mechanisms are flexible membranes made from latex or silicone rubber for example or there can be adjustable seals fitted with sealing gaskets as used in Y adaptors for arterial insertion sheaths. The lumen of the protective tube can be provided with or coated with a small amount of a preferably dry anticoagulant such as heparin or citrate.

The term 'preassembled' means a stent which is attached to the catheter balloon and which is securely fitted to the surface of the catheter balloon. This can, for example, in the case of a steel stent require force to expand it to a greater diameter or in the case of a nitinol stent it can only be prevented from spontaneously expanding to a greater diameter by an appropriate force (e.g. by a covering tube).

The terms 'coated' or 'coating' generally mean a coating that releases active substances and which consists of at least one active substance without any additional additives, or else consists of at least one active substance in a carrier system with further additives such as polymers, oligomers or non-polymeric substances.

These perforated or continuous protective tubes can be moved from the proximal end in the proximal direction when the catheter balloon has reached its required target area; this movement in the proximal direction partially or completely releases the catheter balloon.

The 'distal' end of the catheter or catheter balloon is located at the tip of the catheter (see FIG. 1) and correspondingly the 'proximal' end is the end which is positioned opposite to the distal end. A movement in the proximal direction therefore corresponds to movement in the direction in which the catheter balloon is moved to withdraw it from the body.

According to the invention the protection against expansion, in the form of a tube, cannot be moved in the distal direction if the protection against expansion is not positioned completely over the balloon coated with the active substance. If however the tube is removed from the catheter balloon in a proximal direction before the expansion of the balloon at its desired location, whereby the catheter balloon is completely or at least partially released, then the tube can again be moved translationally in a distal direction up until its position before the dilation took place during the introduction of the catheter balloon into the body.

By means of this movement in a distal direction up to the point where the tube again almost covers the whole of the catheter balloon, then the refolding of the catheter balloon is assisted whereby a smaller cross-sectional area or diameter is achieved compared to when the tube is not pushed over the catheter balloon again.

The protection against expansion in the form of a perforated or continuous tube therefore not only protects the catheter balloon that is coated in the active substance with or without stent during the introduction of the catheter into the body or more precisely into the vessel or the hollow organ or the bodily passage, but also assists in refolding the balloon to again attain a diameter that is close to that at the time of the introduction of the catheter.

In this preferred embodiment the tube is preferably fitted over the entire length of the balloon. The protective tube should be removed from the length of the balloon, or from an even further distance, immediately before the balloon is inflated. If the tube is not pulled back over the entire length of the balloon then only a part of the balloon will be expanded. In order to control the position of the protective tube then, as mentioned above, this can contain radio-opaque markers in the distal region. The relative positions of these markers to similar radio-opaque markers on the balloon shaft are determined before the expansion of the balloon. In this way the doctor can establish the usable length of the balloon immediately before use with an accuracy to the nearest millimetre There can be a stent positioned on the surface of the catheter balloon and underneath the protection against expansion in the form of a perforated or continuous tube. The stents used should preferably be self-expanding stents e.g. nitinol stents, but self expanding stents are not imperative.

Catheters, which have been published, for use in the implantation of self expanding stents, contain a protective tube, as described above. The purpose of the protective tube is initially to maintain the small cross-sectional area of the stent lying along the axis of balloon and which had been compressed to keep this cross-sectional area small. This condition should be maintained until the catheters along with the stents and protective tubes are brought into the position where treatment should take place. When the balloon with the stent is positioned for example in the stenotic section of a blood vessel, the protective tube is then pulled back and the stent is at the same time released. This positions itself against the still constricted vascular wall. Because the restorative force of the self expanding stent is however only very small, the desired diameter of the vascular lumen is frequently not achieved. In these cases the catheter which was originally used is removed from the blood vessel and an additional balloon catheter without a stent is introduced. The balloon is then expanded using high pressure and a contrast medium until the desired vascular diameter is obtained. The balloon can transfer a pharmaceutical substance to the vascular wall by this process. By means of the pharmaceutical substance an undesired thickening of the vascular wall during the healing process is avoided which afterwards ensures that the vessel is held open in the long term.

According to the invention this process can be significantly simplified, it can be organized to be more reliable and more effective where the tube compressing the stent as a protection against expansion also prevents the premature release of the active substance. The novel system consists of the customary catheter which is fitted distally with the usual PTCA or PTA balloon. On the folded balloon a self expanding stent is preferably assembled e.g. form nitinol which is compressed by the tube to a small diameter.

The tube can be pulled back from the proximal end, at least until the stent is released for its entire length. The catheter balloon is at least as long as the stent and in a preferred embodiment is 1 to 10 mm longer at both ends and in a particularly preferred form it is 5 to 10 mm longer.

A significant advantage of this system is that several operations are possible without changing the catheter and that optimum initial and long term results are produced, which are more rapidly obtained, more cost-effective and of better quality than when previously known catheters are used one after another.

Balloon catheters according to the invention can therefore facilitate the implantation of stents, but they are not however necessary. The novel balloon catheters described here can be coated with various materials as required. The coatings are protected against premature release during handling or on the way to the targeted tissue by means of the protections against expansion in particular using solid or more precisely non-perforated tubes, or using continuous tubes.

Furthermore this present invention concerns a balloon catheter coated with an active substance including a solid and/or tube shaped protection against expansion with a self-expanding stent located inside it and including a catheter balloon. Until it is released the protection against expansion protects the stent against premature expansion and protects the balloon against premature loss of the coating material.

Further this present invention concerns a balloon catheter coated with at least one active substance including a tube-shaped and/or solid protection against expansion where the space between the catheter shaft and the protective tube is sealed to prevent penetration of bodily fluids and including a catheter balloon where the protection against expansion protects the catheter balloon against premature expansion and premature loss of the coating material until it is expanded and where the protection against expansion can optionally contain or include a self expanding stent.

In another preferred embodiment the balloon is held together by an elastic tubular or annular mesh, net, coil, trellis or grid. Such structures are also described in US 2006/0085065 but are however loaded with active substances and are themselves used on balloon catheters as carriers of the active substances in combination with preassembled stents.

Furthermore this present invention therefore concerns balloon catheters with a protection against expansion preferably in the form of a flexible band, a flexible network, a flexible grid, a flexible film or a flexible coil.

According to the invention the flexible network, the flexible grid, the flexible film or the flexible coil exercises an opposing force on the longitudinal axis of the catheter balloon. This force is not so strong that the catheter balloon is actually prevented from expanding i.e. this restorative force which is exercised by the protection against expansion in the form of a network, a grid, a film or coil or some other regularly or irregularly perforated mesh is smaller than the pressure that has been produced inside the catheter balloon, so that the protection against expansion stretches to the desired diameter along with the catheter balloon. When the catheter balloon is deflated the restorative force provided by the protection against expansion is however in the same direction as the vacuum produced inside the catheter balloon and contributes to a better and more effective refolding of the catheter balloon.

The catheter balloon is preferably returned to a diameter which is a maximum of 30% greater, and preferably a maximum of 20%, and more preferably a maximum of 10%, and even more preferably a maximum of 8% greater and yet even more preferably 6% greater and still even more preferably is 5% greater than before the expansion i.e. on removing the catheter balloons from the body these FIGURES are the maximum percentage increases in size or in thickness compared to when they were inserted into the body.

Basically the diameter of the catheter balloon with the protection against expansion in the form of a network, a grid, a film or a coil or any other regularly or irregularly perforated mesh after expansion and deflation is smaller than that of a catheter balloon without such protection against expansion following expansion and deflation.

When the balloon is expanded the mesh expands as the wall of the balloon expands. When the balloon is deflated the material surrounding the folded balloon can again adopt almost the same small diameter that it had before the expansion. In this case the significant difference to the stent used to support the vascular wall is that after it had fulfilled its function the tubular or grid-like material surrounding the balloon pulls itself back to almost the same small diameter which it had before the balloon was expanded. After widening the vessel the material is again removed from the vessel along with the balloon. Suitable materials are elastic tear-resistant plastics e.g. latex or elastic metals either with or without shape memory e.g. steel or nitinol.

Because only a small tensile strength and no strength in compression is necessary then significantly smaller material strengths are necessary than those used with the stents. The specifications in terms of biocompatibility are lower, because the materials do not remain in the body.

In a preferred variant the elastic materials are firmly bound to the catheter or more precisely to its shaft. Another preferred embodiment concerns a mesh or some other protective structure with shape memory (as demonstrated by nitinol for example), which surrounds the balloon and protects the structure against any loosening of the folds. In contrast to the self-expanding stents the stable form in this case is however not the form with the large cross-sectional area, but rather that with the small cross-sectional area. When insufflation of the balloon takes place with a significantly increased pressure the model becomes expanded. On deflation the structure again returns to its small diameter by itself and can again be removed along with the catheter by using the catheter insertion sheath.

In a further embodiment the material that protects the folding of the balloon during handling can remain adhering to the vascular wall in the expanded state. The significant difference to the customary stent is in this latter case the low radial strength which is indeed sufficient to prevent material from again detaching from the vascular wall but does not support the vascular wall itself. This permits the selection of materials with lower strengths than those which are used with stents and the use of a large number of less mechanically stable substances which are however biocompatible. Biodegradable materials are particularly favoured.

Examples of biodegradable materials are:

polyvalerolactones, poly-ε-decalactones, polylactonic acid, polyglycolic acid polylactides, polyglycolides, copolymers of polylactides and polyglycolides, poly-ε-caprolactone, polyhydroxybutyric acid, polyhydroxybutyrates, polyhydroxyvalerates, polyhydroxybutyrate-co-valerates, poly(1,4-dioxane-2,3-dione), poly(1,3-dioxane-2-one), poly-p-dioxanone, polyanhydrides, polymaleic acid anhydrides, polyhydroxymethacrylates, fibrin, polycyanoacrylates, polycaprolactone dimethylacrylates, poly-ß-maleic acid polycaprolactone butyl acrylates, multiblock polymers made from oligocaprolactonediols and oligodioxanonediols, poly (ether ester) multiblock polymers, PEG, polybutylene terephtalate, polypivotolactone, polyglycolic acid trimethylcarbonates, polycaprolactone glycolides, poly-γ-ethylglutamate, poly(DTH-iminocarbonate), poly(DTE-co-DT-carbonate), poly(bisphenol A-iminocarbonate), polyorthoesters, polyglycolic acid trimethylcarbonates, polytrimethylcarbonates, polyiminocarbonates, poly(N-vinyl)-pyrrolidone, polyvinyl alcohols, polyesteramides, glycolised polyesters, polyphosphoesters, polyphosphazenes, poly[p-carboxyphenoxy)propane], polyhydroxypentanoic acid, polyanhydrides, polyethylene oxide-propylene oxide, soft polyurethanes, polyether esters, poly(ethylene oxide), polyalkene oxalates, polyorthoesters as well as their copolymers, lipids, carrageenans, fibrinogen, starch, collagen, natural and synthetic polyamino acids, zein, modified zein, polyhydroxyalkanoates, pectic acid, actinic acid, modified and unmodified fibrin, casein, carboxy methyl sulphate, albumen, hyaluronic acid, heparan sulphate, heparin, chondroitin sulphate, dextran, ß-cyclodextrins, copolymers made from PEG and polypropylene glycol, gum arabic, guar, gelatine, collagen, collagen-N-hydroxysuccinimide, lipids, phospholipids, modifications and copolymers and/or mixtures of the previously named substances.

In a further embodiment the catheter balloon can, for example, be secured against unfolding by means of a thin coil shaped band passing around it, or by means of a thread or net passing around it (with regard to the design see also US 2006/0085065). Other arrangements of the thread are also possible. The thread, band or net is attached to the catheter either proximally and/or distally. They can include one or more predetermined breaking points situated anywhere along them, but preferably in the middle of the balloon or in the case of a net at one or at several connecting points. When the balloon is expanded the threads can rip at these points if necessary. The threads or bands can however be made from stretchable material or form an expandable mesh. A significant difference to the covering described in U.S. Pat. No. 5,370,614 is the small amount of actual coverage of the surface of the balloon. When the balloon is expanded contact therefore takes place between the balloon and the vascular wall which occurs over almost the whole surface of the balloon. Suitable materials are synthetic and natural materials with sufficient mechanical strength to hold the folds of the balloon in place, or metals, mixtures of materials or composite materials consisting of several layers of different materials.

Biocompatible materials are preferred which have either very slight thrombogenic effects or no thrombogenic effect at all.

Because in all these applications only small forces are necessary to achieve the desired effect—the prevention of premature loosening of the folds of the balloon—then extremely small materials strengths are sufficient, which for their part only cause a minimal increase in the cross-sectional area of the folded balloon, and in fact even reduce the cross-sectional area, when compared to folding which is loosened by applying a force mechanically. By a minimal increase in size an increase in diameter of ≤200 μm is understood which should preferably be ≤100 μm, more preferably ≤50 μm and the most preferred situation is when there is no increase in the diameter at all.

In the last case the reduction in cross-sectional area of the balloon due to the effects of the force supplied by the protection against expansion is greater than the material strength.

A protection against the protective covering on the balloons or the nets changing their position relative to the balloon and against loss on the way to the stented vessel can be provided tight fitting ring shaped structures proximally and/or distally on the balloon or by making a connection with the proximal grip.

Furthermore the catheter balloon is coated with one or more active substances according to choice together with further additives. In a preferred form the balloon contains one or several active substances which are preferably readily soluble in water or are at least hydrophilic in a soluble or slightly soluble form. In another preferred form particularly lipophilic active substances are used. The additives can be readily soluble or sparingly soluble in water. The active substance or active substances and if required the additives can be located on the balloon membrane, but can also be located between the stent struts or else situated on top of them. The catheter balloon can be coated with an active substance or a mixture of active substances and optionally with further additives. The stent may also be coated in this way. Here the stent and the catheter may be coated with the same active substance or there may be a different active substance on the balloon. By selecting different active substances for the stent and the catheter balloon and also by choosing different additives for the coating on the stent and for the coating on the balloon, then different active substances and different systems for the release of the active substances can be adeptly combined with one another with different release kinetics being produced as a result. For example, in use on the catheter balloon there can preferably be a pure active substance, preferably a hydrophilic active substance together with an optional additive, preferably a non-polymer additive and preferably a hydrophilic additive such as a contrast medium so that the release kinetics for the active substance on the catheter balloon range from rapid to spontaneous. The same active substance or another active substance can however be embedded on the stent in a polymer carrier system so that the release of the active substance on the stent is either delayed or else the release takes place over a long period of time. As a result spontaneous release and long term release can be combined with one another. There is in addition the possibility to provide the stent with a polymer carrier containing at least one active substance for a delayed release and to then provide this polymer carrier with yet another layer of another active substance or preferably the same active substance for a rapid release.

In this way a system is achieved on the stent which allows for the spontaneous release as well as the delayed release of at least one active substance and which together with a coated catheter balloon guarantees the supply of an active substance to the entire surface area of the vascular wall by spontaneous release.

It is furthermore preferred when the catheter balloon is longer than the preassembled stent on which it is mounted i.e. the catheter balloon extends over the distal and proximal ends of the stent. In addition it is preferred when the catheter balloon is also coated with an active substance and optionally with at least one additive in the areas extending beyond the length of the stent so that during stent implantation the areas of the vascular wall bordering the ends of the stent are also receive an adequate supply active substance.

Viscous or dry, pasty coatings are preferred. The dosage of the active substances depends on their strength: preferred dosages are between 0.1 and 10 µg/mm² balloon surface which corresponds to the surface area of the vascular wall which is to be treated. The system is also suitable for use with higher dosages.

The catheter balloon can be coated with a pure active substance, a mixture of active substances or with at least one additive, in the expanded state as well as in the compressed state, specifically placed underneath the folds or else either completely or partially covering the whole surface of the balloon.

In addition the protection against expansion preferably corresponds to a large extent in diameter and in length to the catheter when it is folded together or when it is in its preformed condition and preferably expands over at least the coated area. The protection against expansion itself is however preferably left uncoated.

Furthermore the catheter balloon can be provided with or contain a preassembled stent which returns to a small cross-sectional area or a small diameter after the expansion of the catheter balloon and can be removed from the body along with the catheter balloon.

The term 'remove from the body' is understood to mean removal 'from the vessel, tissue, hollow organ or bodily passage'.

If the protection against expansion is used in the form of a network, a grid, a film, a coil or some other regularly or irregularly perforated mesh, then a stent, which is designed to stay at the location following dilatation can then be crimped onto or otherwise attached to the protection against expansion.

The stent itself can however also serve as a protection against expansion where the protection against expansion is achieved by means of the stent. The usual biostable or biodegradable stents can be used made from metal, metal alloys or plastics. Furthermore stents can be used which exercise no appreciable supporting function following implantation.

Furthermore the catheter balloon and also the stent can be coated with an active substance or a mixture of at least one substance with at least one additive. The coating of the balloons and/or stents is described in many patent specifications and publications e.g. EP 1372737, WO 2004028582, WO 2004022124, WO 2004006976, DE 10 2004 046244.

Suitable active substances are antiproliferative, antiinflammatory, antiphlogistic, anti hyperplastic, antineoplastic, antimitotic, cytostatic, cytotoxic, antiangiogenic, antirestenotic, microtubule inhibiting, antimigration or antithrombotic active substances.

Examples of suitable active substances are:
abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, apocymarin, argatroban, aristolactam-All, aristolochic acid, arsenic and arsenic-containing oxides, salts, chelates and organic compounds, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, boswellic acids and their derivatives, bruceanoles A, B and C, bryophyllin A, busulfan, antithrombin, bivalirudin, cadherins, camptothecin, capecitabine, o-carbamoylphenoxyacetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-Type natriuretic peptide (CNP), cudraisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, dunaimycin, epirubicin, epothilone A and B, erythromycine, estramustine, etoposide, everolimus, filgrastim, fluroblastin, fluvastatin, fludarabine, fludarabin-5'-dihydrogenphosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, bismuth and bismuth compounds or chelates, irinotecan, topotecan, hydroxycarbamide, miltefosine, pentostatine, pegaspargase, exemestane, letrozole, formestane, SMC proliferation inhibitor-2ω, mitoxantrone, mycophenolate mofetil, c-myc antisense, b-myc antisense, ß-lapachone, podophyllotoxin, podophyllic acid-2-ethylhydrazide, molgramostim (rhuGM-CSF), peginterferon α-2b, lanograstim (r-HuG-CSF), macrogol, selectin (cytokin antagonist), cytokin inhibitors, COX-2 inhibitor, NFkB, angiopeptin, monoclonal antibodies which inhibit muscle cell proliferation, bFGF antagonists, probucol, prostaglandins, 1-hydroxy-11-methoxycanthin-6-one, scopolectin, NO donors, pentaerythritol tetranitrate, syndnoimines, S-nitrosoderivatives, tamoxifen, staurosporine, ß-oestradiol, α-oestradiol, oestriol, oestrone, ethinyloestradiol, medroxyprogesterone, oestradiol cypionates, oestradiol benzoates, tranilast, kamebakaurin and other terpenoids, which are used in the treatment of cancer, verapamil, tyrosine kinase inhibitors (tyrphostins), paclitaxel, paclitaxel derivatives, 6-α-hydroxy paclitaxel, 2'-succinylpaclitaxel, 2'-succinylpaclitaxeltriethanolamine, 2'-glutarylpaclitaxel, 2'-glutarylpaclitaxeltriethanolamine, 2'-O-ester of paclitaxel with N-(dimethylaminoethyl)glutamide, 2'-O-ester of paclitaxel with N-(dimethylaminoethyl)glutamidhydrochloride, taxotere, carbon suboxides (MCS), macrocyclic oligomers of carbon suboxide, mofebutazone, lonazolac, lidocaine, ketoprofen, mefenamic acid, piroxicam, meloxicam, penicillamine, hydroxychloroquine, sodium aurothiomalate, oxaceprol, β-sitosterin, myrtecaine, polidocanol, nonivamide, levomenthol, ellipticine, D-24851 (Calbiochem), colcemid, cytochalasin A-E, indanocine, nocadazole, S 100 protein, bacitracin, vitronectin receptor antagonists, azelastine, guanidyl cyclase stimulator tissue inhibitor of metal proteinase1 and 2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active substances from the group of antibiotics such as cefadroxil, cefazolin, cefaclor, cefotixin, tobramycin, gentamycin, penicillins such as dicloxacillin, oxacillin, sulfonamides, metronidazole, enoxoparin, desulphated and N-reacetylated heparin, tissue plasminogen activator, GpIIb/IIIa platelet membrane receptor, factor Xa inhibitor antibodies, heparin, hirudin, r-hirudin, PPACK, protamine, prourokinase, streptokinase, warfarin, urokinase, vasodilators such as dipyramidol, trapidil, nitroprussides, PDGF antagonists such as triazolopyrimidine and seramine, ACE inhibitors such as captopril, cilazapril, lisinopril, enalapril, losartan, thioprotease inhibitors, prostacyclin, vapiprost, interferon a, ß and γ, histamine antagonists, serotonin blockers, apoptosis inhibitors, apoptosis regulators such as p65, NF-kB or Bcl-xL antisense oligonucleotides, halofuginone, nifedipine, tocopherol tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecainide, propafenone, sotolol, naturally and synthetically obtained steroids such as inotodiol, maquiroside A, ghalakinoside, mansonine, strebloside, hydrocortisone, betamethasone, dexamethasone, non-steroidal substances (NSAIDS) such as fenoporfen, ibuprofen, indomethacin, naproxen, phenylbutazone and other antiviral agents such as acyclovir, ganciclovir and zidovudin, clotrimazole, flucytosine, griseofulvin, ketoconazole, miconazole, nystatin, terbinafine, antiprozoal agents such as chloroquine, mefloquine, quinine, furthermore natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N, and P, isodeoxyelephantopin, tomenphantopin A and B, coronarin A, B, C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterin, protoanemonin, cheliburin chloride, sinococuline A and B, dihydronitidine, nitidine chloride, 12-beta-hydroxypregna-dien-3,20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidine, oxoushinsunine, periplocoside A, ursolic acid, deoxypsorospermin, psycorubin, ricin A, sanguinarine, manu wheat acid, methylsorbifolin, sphatheliachromen, stizophyllin, mansonine, strebloside, dihydrousambaraensine, hydroxyusambarine, strychnopentamine, strychnophylline, usambarine, usambarensine, liriodenine, oxoushinsunine, daphnoretin, lariciresinol, methoxylariciresinol, syringaresinol, sirolimus (rapamycin), rapamycin combined with arsenic or with compounds of arsenic or with complexes containing arsenic, somatostatin, tacrolimus, roxithromycin, troleandomycin, simvastatin, rosuvastatin, vinblastine, vincristine, vindesine, thalidomide, teniposide, vinorelbine, trofosfamide, treosulfan, tremozolomide, thiotepa, tretinoin, spiramycin, umbelliferone, desacetylvismione A, vismione A and B, zeorin, fasudil.

Solvents, sugars, vitamins, proteins, polymers, oligomers, contrast media and other physiologically tolerable substances can be used as additives.

The contrast media are mainly substances that contain iodine, manganese, iron, lanthanum, cerium, praseodymium, neodymium, samarium, europium, gadolinium, terbium, dysprosium, holmium, erbium, thulium, ytterbium and/or lutetium. The contrast media usually used for radiography, computer tomography (CT) nuclear spin tomography or magnetic resonance tomography (MRT) can be used as contrast media.

Furthermore contrast media containing iodine are preferred for use when the vessels are imaged (angiography and phlebography) and for use with CT (computer tomography). Contrast media containing a 1,3,5 iodosubstituted benzene nucleus, radiocontrast agents, diatrizoic acid, iothalamic acid, iotrolan, iodixanol, iopamidol, iohexol, iomeprol, iopromide and iotroxic acid or readily soluble or less readily soluble salts of the acids concerned.

Paramagnetic contrast media represent a further class of preferred contrast media which generally contain a lanthanide. Among these paramagnetic contrast media which have unpaired electrons there is, for example, gadolinium ($Gd^{3+}$), which has a total of seven unpaired electrons. Europium ($Eu^{2+}$, $Eu^{3+}$) dysprosium ($Dy^{3+}$) and holmium ($Ho^{3+}$) also belong to this group. These lanthanides can also be used in chelated form by using for example polycarbon acids and polyaza acids, particularly EDTA, DTPA and DOTA as chelating agents. Examples of contrast media that contain gadolinium are gadolinium-diethylenetriaminepentaacetic acid (also known as gadopentetic acid or GdDPTA), gadodiamide, meglumine gadoterate, gadoteridol and gadobutrol.

Balloon catheters according to the invention, with or without the stent attached and with or without a coating can be used for the localized treatment and prophylaxis of vascular diseases and for the treatment of changes to the vascular walls which do not significantly restrict the flow of blood. Balloon catheters according to the invention are particularly suitable for the treatment and prophylaxis of stenosis, restenosis, in-stent stenosis and arteriosclerosis.

EXAMPLES

Example 1

FIG. 1 shows a coated balloon underneath a self-expanding stent

The system consists of a balloon catheter fitted with a balloon of diameter 5 mm, length 100 mm and coated with 3 µg paclitaxel/mm² balloon surface area. Over the balloon there is a self-expanding nitinol stent (5 mm×80 mm) in its non-expanded condition which is compressed to a small diameter by a tube fitted as a protection against expansion which can be pulled back by the user.

When the balloon with the stent is located in the stenotic section of the blood vessel, the tube is then pulled back and releases the stent. This comes up against the still constricted vascular wall. The balloon is then expanded with high pressure and using a contrast medium until the original diameter of the vessel is achieved. During this process the balloon transfers the active substance onto the vascular wall. In this way any undesirable thickening of the vascular wall during the healing process is avoided and the vessel can be kept open for a long period of time.

After the stent has been successfully positioned and following dilatation the catheter balloon is again deflated the contrast medium is extracted by suction and by using the applied vacuum. To achieve the original diameter the tube can again be pushed over the catheter balloon in a distal direction. Afterwards the catheter balloon is removed from the blood vessel.

Example 2

The folded balloon (4.0×40 mm) of a balloon catheter, which is coated with 7 µg methotrexate/mm² balloon surface area, is enveloped in a coil-shaped PTFE band 10 µm thick and 200 µm wide in such a way that the distance between the turns of the band is 3 mm. The band is firmly attached to the catheter shaft at both the balloon's proximal and distal ends. The band does not produce a measurable increase in the diameter of the folded balloon. On expanding the balloon at the location of the constriction of the blood vessel the band rips apart anywhere without the ends of the band losing contact with the catheter shaft. At the end of the treatment it is removed from the treated blood vessel along with the catheter.

Example 3

A balloon catheter (5 mm balloon diameter, 120 mm balloon length) coated with a pharmaceutical substance is introduced in its folded condition into a PTFE tube of 1.6 mm external diameter and 1.3 mm internal diameter so that the distal end of the balloon catheter with the catheter tip and the opening to the central channel of the catheter shaft (to later receive the guide wire) just protrudes from out of the PTFE tube. The balloon coated with the active substance is situated completely within the lumen of the PTFE tube. Ultravist 370 (Bayer Schering Pharma AG, Berlin) corresponds to a solution of 0.77 iopromide/ml. Using an injection needle 4 µl of this contrast medium Ultravist 370 is placed distally into the lumen between the wall of the PTFE tube and the catheter tip. The tube is stored for 24 hours at 30° C. Afterwards there is a plug of solid contrast medium which firmly seals the approximately 3 mm long section of the PTFE tube. The system is sterilised in the usual way using ethylene oxide.

Testing the effectiveness of the seal:

The distal end of the tube is placed in blood which has been warmed to 40° C. and is then moved rhythmically. It should take around 5 minutes before the plug of contrast medium has dissolved to such an extent that blood can penetrate into the protective tube.

If it is required the contrast medium plug can be pushed from the PTFE tube with the balloon catheter or else it can also be released prematurely by pulling back either the catheter or the tube. Should the contrast medium plug be located outside the protective tube and if it is surrounded by blood on all sides then it should dissolve completely within seconds up to a maximum time of 1 minute.

The invention claimed is:

1. A balloon catheter comprising:
    a catheter shaft;
    a protective tube on the catheter shaft, wherein the protective tube comprises a distal end and a proximal end;
    a self expanding stent located inside the protective tube;
    a catheter balloon located inside the protective tube;
    at least one active substance located between the catheter balloon and the protective tube;
    a seal located in the protective tube proximate the distal end of the protective tube and between the protective tube and the catheter shaft, wherein the seal prevents penetration of bodily fluids between the protective tube and the catheter shaft, and wherein the seal comprises a pharmaceutical and physiologically inactive substance in solid form that is soluble in blood, wherein the seal is configured to dissolve such that blood can penetrate into the protective tube within five minutes of placement of the seal and the protective tube in blood;
    the protective tube compresses the self expanding stent to protect against premature expansion of the self expanding stent and against premature loss of the at least one active substance.

2. The balloon catheter of claim 1, wherein the protective tube comprises a radio-opaque marker at the distal end or at the proximal end, or at both the distal end and the proximal end.

3. The balloon catheter of claim 2, wherein the catheter balloon comprises a radio-opaque marker.

4. The balloon catheter of claim 1, wherein the protective tube is movable in a proximal direction and wherein the protective tube, when moved in a proximal direction, completely or partially releases the catheter balloon.

5. The balloon catheter of claim 4, wherein the protective tube is movable in a distal direction after being moved in the proximal direction, and wherein the protective tube, when moved in the distal direction, surrounds the catheter balloon.

6. The balloon catheter of claim 1, wherein the protective tube is removable together with the catheter balloon after expansion of the catheter balloon.

7. The balloon catheter of claim 1, wherein the self expanding stent is a preassembled stent configured to resume a small diameter following expansion of the catheter balloon and the preassembled stent is removable with the balloon catheter.

8. The balloon catheter of claim 1, wherein the seal comprises contrast media.

9. The balloon catheter of claim 1, wherein the at least one active substance comprises a coating on the catheter balloon.

10. The balloon catheter of claim 1, wherein the at least one active substance is provided on self expanding stent.

11. The balloon catheter of claim 1, wherein a coating on the catheter balloon comprises the at least one active substance, and wherein a different active substance is provided on the self expanding stent.

12. The balloon catheter of claim 1, wherein the self expanding stent comprises at least one active substance.

13. A balloon catheter comprising:
    a catheter shaft;
    a protective tube;

a seal located in the protective tube proximate a distal end of the protective tube and between the protective tube and the catheter shaft, wherein the seal prevents penetration of bodily fluids between the protective tube and the catheter shaft, and wherein the seal comprises a pharmaceutical and physiologically inactive substance in solid form that is soluble in blood, wherein the seal is configured to dissolve such that blood can penetrate into the protective tube within five minutes of placement of the seal and the protective tube in blood;

a catheter balloon located in the protective tube; and at least one active substance located between the catheter balloon and the protective tube;

wherein the protective tube compresses the catheter balloon to protect the catheter balloon against premature expansion and against premature loss of the at least one active sub stance;

wherein the protective tube is movable in a proximal direction and wherein the protective tube, when moved in a proximal direction, completely or partially releases the catheter balloon;

and wherein the protective tube is movable in a distal direction after being moved in the proximal direction and after the catheter balloon has been expanded, and wherein the protective tube, when moved in the distal direction, surrounds the catheter balloon after the catheter balloon has been expanded.

14. The balloon catheter of claim 13, wherein the protective tube comprises a radio-opaque marker at the distal end or at the proximal end, or at both the distal end and the proximal end.

15. The balloon catheter of claim 14, wherein the catheter balloon comprises a radio-opaque marker.

16. The balloon catheter of claim 13, wherein the protective tube is removable together with the catheter balloon after expansion of the catheter balloon.

17. The balloon catheter of claim 13, wherein the seal comprises contrast media.

18. The balloon catheter of claim 13, wherein the at least one active substance comprises a coating on the catheter balloon.

* * * * *